United States Patent
Yagita et al.

(10) Patent No.: US 10,315,930 B2
(45) Date of Patent: Jun. 11, 2019

(54) METHOD AND SYSTEM FOR REMOTELY MONITORING A GROUP OF CIRCULATING-WATER UTILIZATION SYSTEMS

(71) Applicant: MITSUBISHI HITACHI POWER SYSTEMS, LTD., Yokohama-shi, Kanagawa (JP)

(72) Inventors: Hiroyuki Yagita, Tokyo (JP); Junichi Minamiura, Tokyo (JP); Jun Hyodo, Tokyo (JP); Yukinobu Yokota, Tokyo (JP); Hayato Shin, Tokyo (JP); Riki Kitagawa, Tokyo (JP)

(73) Assignee: MITSUBISHI HITACHI POWER SYSTEMS, LTD., Yokohama-shi (JP)

( * ) Notice: Subject to any disclaimer, the term of this patent is extended or adjusted under 35 U.S.C. 154(b) by 294 days.

(21) Appl. No.: 15/037,601

(22) PCT Filed: Dec. 4, 2014

(86) PCT No.: PCT/JP2014/082094
§ 371 (c)(1),
(2) Date: May 18, 2016

(87) PCT Pub. No.: WO2015/083782
PCT Pub. Date: Jun. 11, 2015

(65) Prior Publication Data
US 2016/0289087 A1    Oct. 6, 2016

(30) Foreign Application Priority Data
Dec. 5, 2013    (JP) .................................. 2013-251622

(51) Int. Cl.
*C02F 1/00*    (2006.01)
*E03B 1/04*    (2006.01)
(Continued)

(52) U.S. Cl.
CPC ................ *C02F 1/008* (2013.01); *E03B 1/04* (2013.01); *E03B 1/042* (2013.01); *G01N 33/18* (2013.01);
(Continued)

(58) Field of Classification Search
CPC ......... C02F 2201/008; E03B 2001/047; G01N 33/18
See application file for complete search history.

(56) References Cited

U.S. PATENT DOCUMENTS 3,558,255 A    1/1971   Rose
3,638,490 A    2/1972   Buettner
(Continued)

FOREIGN PATENT DOCUMENTS

JP    S61-230707 A    10/1986
JP    S63-119892 A    5/1988
(Continued)

OTHER PUBLICATIONS

International Search Report dated Jan. 20, 2015, issued in counterpart International Application No. PCT/JP2014/082094, with partial translation. (8 pages). (U.S. Appl. No. 15/037,601).
(Continued)

*Primary Examiner* — Mohamed Charioui
(74) *Attorney, Agent, or Firm* — Westerman, Hattori, Daniels & Adrian, LLP

(57) ABSTRACT

A method of remotely monitoring a group of circulating-water utilization systems comprising a plurality of circulating-water utilization systems 1, includes: an operational-ratio detection step of detecting operational ratios of treatment vessels forming a treatment-vessel row of a purifying unit 8, for each of the plurality of circulating-water utilization systems constituting the group of circulating-water utilization systems; a data transmission step of trans-
(Continued)

mitting data related to the operational ratios of the treatment vessels detected in the operational-ratio detection step via a transmission line 60; a data reception step of receiving the data related to the operational ratios of the treatment vessels transmitted in the data transmission step; and a data display step of displaying the data related to the operational ratios of the treatment vessels received in the data reception step.

3 Claims, 10 Drawing Sheets

(51) Int. Cl.
*G01N 33/18* (2006.01)
*C02F 103/00* (2006.01)

(52) U.S. Cl.
CPC .. *C02F 2103/001* (2013.01); *C02F 2103/002* (2013.01); *C02F 2201/008* (2013.01); *C02F 2209/008* (2013.01); *C02F 2307/14* (2013.01); *E03B 2001/045* (2013.01); *E03B 2001/047* (2013.01)

(56) References Cited

U.S. PATENT DOCUMENTS

| | | | |
|---|---|---|---|
| 4,335,606 | A | 6/1982 | Michalak |
| 5,186,052 | A | 2/1993 | Gray |
| 5,817,231 | A | 10/1998 | Souza |
| 5,873,996 | A | 2/1999 | Rozelle et al. |
| 5,958,240 | A | 9/1999 | Hoel |
| 6,015,496 | A | 1/2000 | Khudenko |
| 6,488,853 | B1 | 12/2002 | Mullerheim |
| 6,766,822 | B2 | 7/2004 | Walker |
| 6,783,679 | B1 | 8/2004 | Rozich |
| 8,141,584 | B1 | 3/2012 | Ellyson et al. |
| 8,216,455 | B1 | 7/2012 | O'Brien |
| 8,518,262 | B2 | 8/2013 | Watkins et al. |
| 8,747,664 | B2 | 6/2014 | Dier |
| 2002/0079267 | A1 | 6/2002 | Savage et al. |
| 2002/0179514 | A1 | 12/2002 | Anderson et al. |
| 2004/0144704 | A1 | 7/2004 | Johnson |
| 2006/0163165 | A1 | 7/2006 | Frank |
| 2006/0254352 | A1 | 11/2006 | Nivens et al. |
| 2007/0012628 | A1 | 1/2007 | Frank |
| 2007/0119247 | A1 | 5/2007 | Nivens et al. |
| 2007/0241041 | A1 | 10/2007 | Shimamura et al. |
| 2008/0152782 | A1 | 6/2008 | Avgoustopoulos et al. |
| 2009/0020172 | A1 | 1/2009 | Walker |
| 2009/0057239 | A1 | 3/2009 | Walker |
| 2009/0107915 | A1 | 4/2009 | Skinner et al. |
| 2009/0127190 | A1 | 5/2009 | Ong et al. |
| 2010/0163489 | A1 | 7/2010 | Bauder et al. |
| 2010/0282654 | A1 | 11/2010 | Hauschild |
| 2010/0307984 | A1 | 12/2010 | Mortensen et al. |
| 2011/0068058 | A1 | 3/2011 | Sun |
| 2011/0089036 | A1 | 4/2011 | Sparrow et al. |
| 2011/0186510 | A1 | 8/2011 | Whiteman |
| 2011/0284433 | A1 | 11/2011 | Shah et al. |
| 2011/0303310 | A1 | 12/2011 | Klicpera |
| 2011/0303311 | A1 | 12/2011 | Klicpera |
| 2012/0164064 | A1* | 6/2012 | Guillou .............. C01B 3/32 423/650 |
| 2012/0285895 | A1 | 11/2012 | Smiddy |
| 2013/0001142 | A1 | 1/2013 | Novak et al. |
| 2013/0008260 | A1 | 1/2013 | Polczynski |
| 2013/0020266 | A1* | 1/2013 | Timmons ............ A01K 63/045 210/786 |
| 2013/0105415 | A1 | 5/2013 | Xia et al. |
| 2013/0240420 | A1 | 9/2013 | Robertson et al. |
| 2013/0284679 | A1 | 10/2013 | Bailin et al. |
| 2013/0297529 | A1 | 11/2013 | Shirazi |
| 2016/0319522 | A1 | 11/2016 | Sparre et al. |

FOREIGN PATENT DOCUMENTS

| | | |
|---|---|---|
| JP | H06-79142 A | 3/1994 |
| JP | H06-210291 A | 8/1994 |
| JP | H06-226059 A | 8/1994 |
| JP | H06-240711 A | 8/1994 |
| JP | H06-269766 A | 9/1994 |
| JP | H06-277455 A | 10/1994 |
| JP | 06-77886 U | 11/1994 |
| JP | H07-68257 A | 3/1995 |
| JP | 7-251186 A | 10/1995 |
| JP | 08-19773 A | 1/1996 |
| JP | H08-229590 A | 9/1996 |
| JP | H09-296493 A | 11/1997 |
| JP | H10-33953 A | 2/1998 |
| JP | H10-57941 A | 3/1998 |
| JP | 10-286033 A | 10/1998 |
| JP | 11-090464 A | 4/1999 |
| JP | H11-114551 A | 4/1999 |
| JP | H11-207155 A | 8/1999 |
| JP | H11-220155 A | 8/1999 |
| JP | 2000-288570 A | 10/2000 |
| JP | 2001-170458 A | 6/2001 |
| JP | 2002-045872 A | 2/2002 |
| JP | 2002-166263 A | 6/2002 |
| JP | 2002-210335 A | 7/2002 |
| JP | 2002-215731 A | 8/2002 |
| JP | 2002-267657 A | 9/2002 |
| JP | 2002-316143 A | 10/2002 |
| JP | 2003-019491 A | 1/2003 |
| JP | 2003-075209 A | 3/2003 |
| JP | 2003-088891 A | 3/2003 |
| JP | 2003-178155 A | 6/2003 |
| JP | 2003-519552 A | 6/2003 |
| JP | 2004-008958 A | 1/2004 |
| JP | 2004-038902 A | 2/2004 |
| JP | 2004-041887 A | 2/2004 |
| JP | 2004-141846 A | 5/2004 |
| JP | 2004-249174 A | 9/2004 |
| JP | 2004-290719 A | 10/2004 |
| JP | 2005-149003 A | 6/2005 |
| JP | 2005-186960 A | 7/2005 |
| JP | 2006-051477 A | 2/2006 |
| JP | 2006-223935 A | 8/2006 |
| JP | 2006-233779 A | 9/2006 |
| JP | 2006-281074 A | 10/2006 |
| JP | 2006-281159 A | 10/2006 |
| JP | 2006-302049 A | 11/2006 |
| JP | 2006-305499 A | 11/2006 |
| JP | 2006-310209 A | 11/2006 |
| JP | 2007-185648 A | 7/2007 |
| JP | 2008-307503 A | 12/2008 |
| JP | 2009-073763 A | 4/2009 |
| JP | 2009-124800 A | 6/2009 |
| JP | 2009-153784 A | 7/2009 |
| JP | 2010-120015 A | 6/2010 |
| JP | 2010-188344 A | 9/2010 |
| JP | 2010-253355 A | 11/2010 |
| JP | 2010-538823 A | 12/2010 |
| JP | 4611120 B2 | 1/2011 |
| JP | 2011-078979 A | 4/2011 |
| JP | 2011-152544 A | 8/2011 |
| JP | 2011-189253 A | 9/2011 |
| JP | 2012-092579 A | 5/2012 |
| JP | 2012-106198 A | 6/2012 |
| JP | 5116986 B2 | 1/2013 |
| JP | 2013-034926 A | 2/2013 |
| JP | 2013-043153 A | 3/2013 |
| JP | 2013-188710 A | 9/2013 |
| WO | 2013/176119 A1 | 11/2013 |

OTHER PUBLICATIONS

Office Action dated Mar. 4, 2014, issued in counterpart Japanese Patent Application No. 2013-251621, with English translation. (5 pages), (U.S. Appl. No. 15/100,849).

(56) References Cited

OTHER PUBLICATIONS

International Search Report dated Jan. 27, 2015, issued in International Patent Application No. PCT/JP2014/082096. (9 pages), (U.S. Appl. No. 15/100,849).
Notification of Transmittal of Translation of the International Preliminary Report on Patentability (Form PCT/IB/338) of International Application No. PCT/JP2014/082096 dated Jun. 16, 2016, with Forms PCT/IB/373 and PCT/ISA/237. (13 pages) (U.S. Appl. No. 15/100,849).
Translation of Notification of Transmittal of Translation of the International Preliminary Report on Patentability (Form PCT/IB/338) of International Application No. PCT/JP2014/082097 dated Jun. 16, 2016, with Forms PCT/IB/373 and PCT/ISA/237. (15 pages), (U.S. Appl. No. 15/100,884).
International Search Report dated Feb. 10, 2015, issued in International Patent Application No. PCT/JP2014/082098. (7 pages).
Notice of Allowance of counterpart Japanese Application No. 2013-251619, dated May 16, 2014, with English translation. (6 pages). (U.S. Appl. No. 15/100,884).
Notice of Allowance of counterpart Japanese Application No. 2013-251620, dated Mar. 4, 2014, with English translation. (6 pages).
Notice of Allowance of counterpart Japanese Application No. 2013-251621, dated Feb. 25, 2014, with English translation. (6 pages). (U.S. Appl. No. 15/100,849).
Translation of Notification of Transmittal of Translation of the International Preliminary Report on Patentability (Form PCT/IB/338) of International Application No. PCT/JP2014/082094, dated Jun. 16, 2016, with Forms PCT/IB/373 and PCT/ISA/237. (11 pages). (U.S. Appl. No. 15/037,601).
Notice of Allowance of counterpart Japanese Application No. 2013-251622, dated May 23, 2014, with English translation. (6 pages). (U.S. Appl. No. 15/037,601).
Translation of Notification of Transmittal of Translation of the International Preliminary Report on Patentability (Form PCT/IB/338) of International Application No. PCT/JP2014/082098 dated Jun. 16, 2016, with Forms PCT/IB/373 and PCT/ISA/237. (11 pages).
International Search Report dated Feb. 10, 2015, issued in International Patent Application No. PCT/JP2014/082097. (8 pages). (U.S. Appl. No. 15/100,884).
Notice of Allowance dated Aug. 4, 2017, issued in U.S. Appl. No. 15/100,884 (36 pages).
Notice of Allowance dated Nov. 23, 2016, issued in related U.S. Appl. No. 15/100,849 (9 pages).
Notification of Transmittal of Translation of the International Preliminary Report on Patentability (Form PCT/IB/338) of International Application No. PCT/JP2014/082082 dated Jun. 16, 2016, with Forms PCT/IB/373 and PCT/ISA/237. (11 pages).
International Search Report dated Jan. 13, 2015, issued in counterpart International Application No. PCT/JP2014/082082. (8 pages).
Decision to Grant a Patent dated May 7, 2014, issued in counterpart Japanese Patent Application No. 2013-251625, with English translation, (6 pages).
Office Action dated Feb. 12, 2014, issued in counterpart Japanese Patent Application No. 2013-251630, with English translation. (7 pages).
Decision to Grant a Patent dated May 7, 2014, issued in counterpart Japanese Patent Application No. 2013-251630, with English translation. (6 pages).
International Search Report dated Jan. 13, 2015, issued in counterpart International Application No. PCT/JP2014/082079. (8 pages).
Notification of Transmittal of Translation of the International Preliminary Report on Patentability (Form PCT/IB/338) of International Application No. PCT/JP2014/082079 dated Jun. 16, 2016, with Forms PCT/IB/373 and PCT/ISA/237. (13 pages).
Decision to Grant a Patent dated Mar. 4, 2014, issued in counterpart Japanese Patent Application No. 2013-251627, with English translation. (6 pages).

International Search Report dated Jan. 13, 2015, issued in counterpart International Application No. PCT/JP2014/082080. (7 pages).
Notification of Transmittal of Translation of the International Preliminary Report on Patentability (Form PCT/IB/338) of International Application No. PCT/JP2014/082080 dated Jun. 16, 2016, with Forms PCT/IB/373 and PCT/ISA/237. (11 pages).
Decision to Grant a Patent dated May 23, 2014, issued in counterpart Japanese Patent Application No. 2013-251626, with English translation. (6 pages).
International Search Report dated Jan. 13, 2015, issued in counterpart International Application No. PCT/JP2014/082081. (9 pages).
Notification of Transmittal of Translation of the International Preliminary Report on Patentability (Form PCT/IB/338) of International Application No. PCT/JP2014/082081 dated Jun. 16, 2016, with Forms PCT/IB/373 and PCT/ISA/237. (15 pages).
International Search Report dated Jan. 13, 2015, issued in counterpart International Application No. PCT/JP2014/062083 (7 pages).
Notification of Transmittal of Translation of the International Preliminary Report on Patentability (Form PCT/IB/338) of International Application No. PCT/JP2014/082083 dated Jun. 16, 2016, with Forms PCT/IB/373 and PCT/ISA/237. (11 pages).
Decision to Grant a Patent dated Feb. 25, 2014, issued in counterpart Japanese Patent Application No. 2013-251624, with English translation. (6 pages).
International Search Report dated Jan. 20, 2015, issued in counterpart International Application No. PCT/JP2014/082093 (7 pages).
Notification of Transmittal of Translation of the International Preliminary Report on Patentability (Form PCT/IB/338) of International Application No. PCT/JP2014/082093 dated Jun. 16, 2016, with Forms PCT/IB/373 and PCT/ISA/237. (11 pages).
Decision to Grant a Patent dated Mar. 4, 2014, issued in counterpart Japanese Patent Application No. 2013-251623, with English translation. (6 pages).
International Search Report dated Feb. 24, 2015, issued in International App. No. PCT/JP2014/082095. (12 pages).
Notification of Transmittal of Translation of the International Preliminary Report on Patentability (Form PCT/IB/338) of International Application No. PCT/JP2014/082095 dated Jun. 16, 2016, with Forms PCT/IB/373 and PCT/ISA/237. (22 pages).
Decision to Grant a Patent dated Aug. 1, 2014, issued in counterpart Japanese Patent Application No. 2013-251629, with English translation. (6 pages).
International Search Report dated Sep. 10, 2013, issued in International App. No. PCT/JP2013/068920. (7 pages).
Notification of Transmittal of Translation of the International Preliminary Report on Patentability (Form PCT/IB/338) of International Application No. PCT/JP2013/068920 dated Sep. 10, 2013, with Forms PCT/IB/373 and PCT/ISA/237. (10 pages).
Decision to Grant a Patent dated Aug. 12, 2013, issued in counterpart Japanese Patent Application No. 2013-143642, with English translation. (6 pages).
International Search Report dated Sep. 10, 2013, issued in International App. No. PCT/JP2013/068923. (7 pages).
Notification of Transmittal of Translation of the International Preliminary Report on Patentability (Form PCT/IB/338) of International Application No. PCT/JP2013/068923 dated Jan. 12, 2016, with Forms PCT/IB/373 and PCT/ISA/237. (10 pages).
Decision to Grant a Patent dated Aug. 12, 2013, issued in counterpart Japanese Patent Application No. 2013-143843, with English translation. (6 pages).
"Ministry of the Environment", Manual for Industrial Wastewater Treatment Technology Transfer 2002, Mar. 2003, with a concise explanation of the relevance. (133 pages).
Japan Patent Office, Hyojun Gijutsushu (Mizu Shori Gijutsu), May 12, 2006, pp. 94-95.
Notification of Transmittal of Translation of the International Preliminary Report on Patentability (Form PCT/IB/338) of International Application No. PCT/JP2014/082078 dated Jun. 16, 2016, with Forms PCT/IB/373 and PCT/ISA/237. (11 pages).
International Search Report dated Feb. 10, 2015, issued in International App. No. PCT/JP2014/082078. (8 pages).

(56) References Cited

OTHER PUBLICATIONS

Decision to Grant a Patent dated Mar. 4, 2014, issued in counterpart Japanese Patent Application No. 2013-251628, with English translation. (6 pages).
Notice of Allowance of counterpart Japanese Application No. 2013-251620, dated Feb. 25, 2016, with English translation. (6 pages) (U.S. Appl. No. 15/100,865).
Notice of Allowance of counterpart Japanese Application No. 2013-251621, dated May 23, 2014, with English translation. (6 pages). (U.S. Appl. No. 15/100,849).
Notice of Allowance of counterpart Japanese Application No. 2013-251622, dated Mar. 24, 2014, with English translation. (6 pages).
Non-Final Office Action dated Aug. 2, 2018, issued in U.S. Appl. No. 15/100,865 (76 pages).

\* cited by examiner

FIG. 4
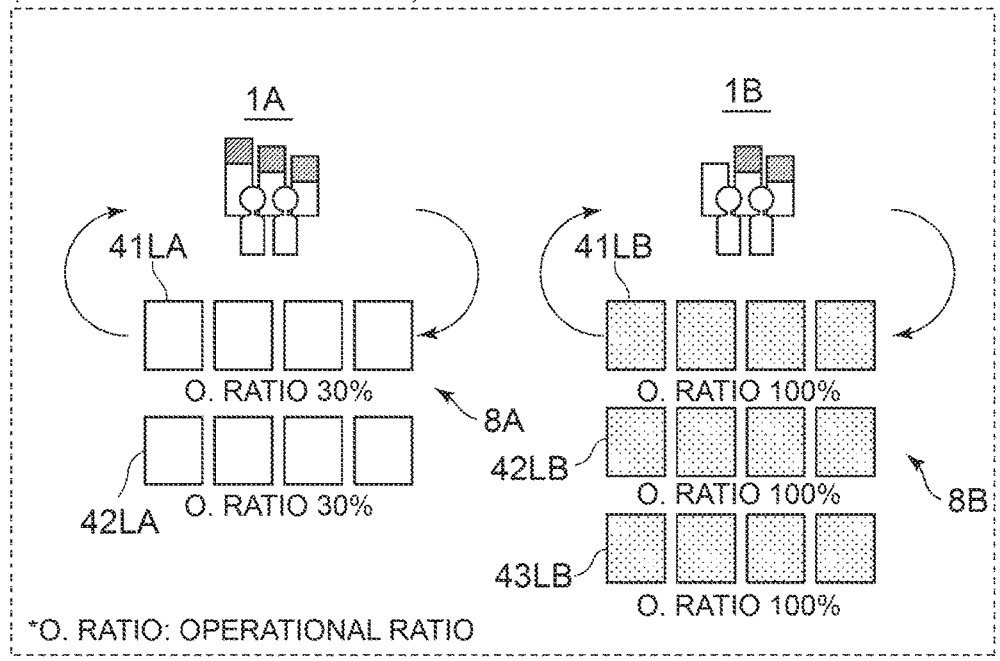
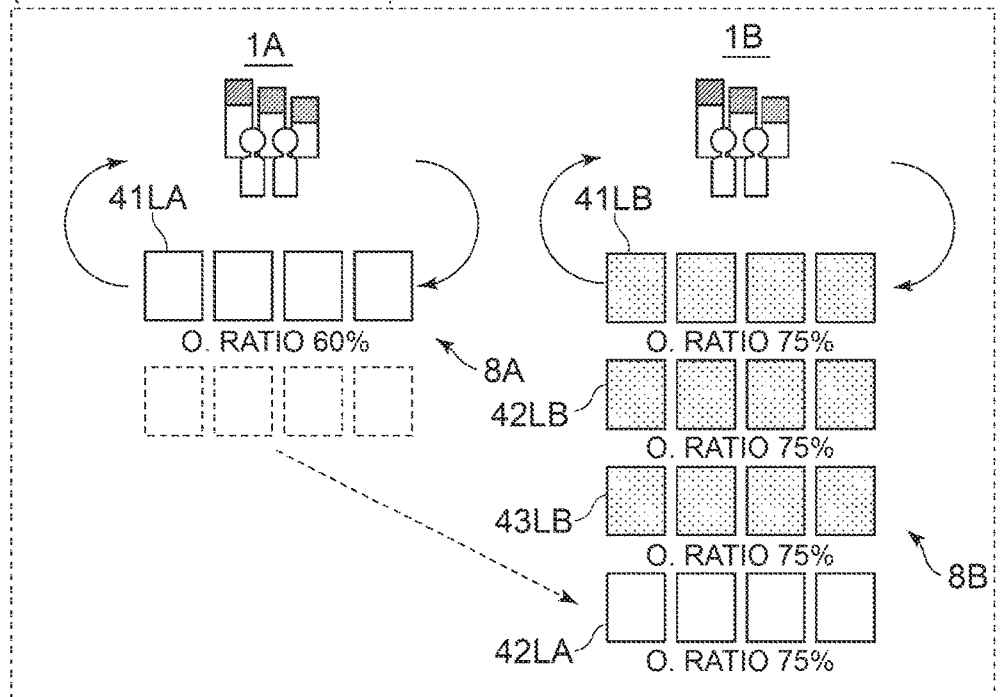

METHOD AND SYSTEM FOR REMOTELY MONITORING A GROUP OF CIRCULATING-WATER UTILIZATION SYSTEMS

TECHNICAL FIELD

The present disclosure relates to a method and a system for remotely monitoring a group of circulating-water utilization systems composed of a plurality of circulating-water utilization systems to be constructed in a specific area separately from a public waterworks system.

BACKGROUND ART

To make the most of limited water resources, a system for purifying and re-utilizing wastewater discharged from buildings, residences, and the like has been known. For instance, Patent Document 1 discloses a wastewater re-utilization system configured to use drainage of clean water used in a household or the like and rainwater for flushing toilets, for instance, whereby it is possible to save water. Further, Patent Document 2 discloses an interior greening system for utilizing gray water, which produces gray water by processing wastewater from a building and re-utilizes the produced gray water to water plants which are grown inside a building.

CITATION LIST

Patent Literature

Patent Document 1: JPH8-19773A
Patent Document 2: JPH10-286033A

SUMMARY

Problems to be Solved

Meanwhile, the applicant is developing a novel circulating-water utilization system having a totally different scale from that of the above described typical re-utilization systems.

The above described typical re-utilization systems are fundamentally intended to purify wastewater of clean water supplied from a waterworks system to utilize the wastewater as gray water for a specific usage in a single building or a single household, for instance, and the used gray water is discharged to a sewage system. In other words, the typical systems require existing public waterworks systems and sewer systems as a premise, and cannot replace the existing systems.

In contrast, the novel circulating-water utilization system that the applicant is now working on is, as described in detail below, a system that provides a service of processing clean water and sewage integrally for an area or a complex inhabited by as many as ten thousand people. In the area or the complex, water is supplied and processed in circulation. In other words, this circulating-water utilization system is designed to be supplied with water from a waterworks system only for drinking purpose for a while, and provided fundamentally as a small distributed system of processing clean water and sewage integrally, constructed independently from existing waterworks systems and sewerage systems.

To expand use of the novel circulating-water utilization systems in a broad region, there has been an issue of how to efficiently resolve unbalance between supply and demand among a plurality of circulating-water utilization systems which are spread out over a broad region.

At least one embodiment of the present invention was made in view of the above typical problem, and an object of the at least one embodiment is to provide a method and a system of monitoring a plurality of circulating-water utilization systems remotely, for efficiently resolving unbalance between supply and demand among a plurality of circulating-water utilization systems spread out over a broad region to expand use of the novel circulating-water utilization system in a broad region.

Solution to the Problems

A method, according to at least one embodiment of the present invention, of remotely monitoring a group of circulating-water utilization systems comprising a plurality of circulating-water utilization systems each of which at least comprises: a circulation channel through which circulating water flows; a discharge channel through which wastewater discharged from a water consumer is discharged to the circulation channel the water consumer being composed of a plurality of water consuming members including at least one of a residence, a tenant shop, or an office which uses the circulating water flowing through the circulating channel; a purifying unit comprising a treatment-vessel row including a plurality of treatment vessels connected in a row, the treatment vessels comprising containers which house treatment devices configured to perform respective treatment processes which constitute a purifying process of purifying the circulating water containing the wastewater flowing through the circulation channel; and a supply channel configured to supply the circulating water purified by the purifying unit to the water consumer, comprises: an operational-ratio detection step of detecting operational ratios of the treatment vessels forming the treatment-vessel row of the purifying unit, for each of the plurality of circulating-water utilization systems constituting the group of circulating-water utilization systems; a data transmission step of transmitting data related to the operational ratios of the treatment vessels detected in the operational-ratio detection step via a transmission line; a data reception step of receiving the data related to the operational ratios of the treatment vessels transmitted in the data transmission step; and a data display step of displaying the data related to the operational ratios of the treatment vessels received in the data reception step.

In the novel circulating-water utilization system being developed by the present applicant, a purifying unit for purifying waste water comprises container-type treatment vessels which include containers each of which houses a treatment device that performs a treatment step constituting a series of purifying steps. This purifying unit includes a treatment-vessel row including a container-type treatment vessel that performs the first treatment step, a container-type treatment vessel that performs the second treatment step, and a container type treatment vessel that performs the third treatment step carried into a site, and connected in series. Such a container-type treatment vessel can be loaded onto a thick to be transported as it is, and thus has a high transportability. Further, such a container-type treatment vessel is housed in a container housing removably, and thus can be installed and removed as desired.

With regard to processing capacity, the above container-type treatment vessels are each supposed to be capable of processing wastewater from approximately 1,000 persons. Thus, to introduce the present circulating-water utilization system to an area or a complex inhabited by as many as 10,000 persons, for instance, a plurality of (e.g. ten) treatment vessels that performs the same treatment process is required. With a plurality of treatment vessels that performs the same treatment process provided as described above, it is possible to reduce processing capacity per treatment vessel. Thus, it is possible to flexibly address population variation in a target area or seasonal variation of water demand. Further, a substitute treatment vessel can be prepared readily, and maintainability is improved.

To launch such novel circulating-water utilization systems in a broad region, according to the above method of remotely monitoring a group of circulating-water utilization systems, operational ratios of the treatment vessels of the purifying unit are detected for each of the plurality of circulating-water utilization systems consisting a group of circulating-water utilization systems, and the data related to the operational ratios is transmitted and collectively displayed at a remote place. Accordingly, it is possible to use the data to determine whether to move a treatment vessel from a purifying unit of a circulating-water utilization system with a low operational ratio of treatment vessels to a purifying unit of a circulating-water utilization system with a high operational ratio to treatment vessels, which makes it possible to efficiently resolve unbalance between supply and demand in a plurality of circulating-water utilization systems which are spread out over a broad region.

In some embodiments, the method further comprises a treatment-vessel moving step of moving the treatment vessel from the purifying unit of one of the circulating-water utilization systems having a detected operational ratio lower than a first threshold set in advance, to the purifying unit of another one of the circulating-water utilization systems having a detected operational ratio higher than a second threshold which is set to be greater than the first threshold, from among the plurality of circulating-water utilization systems constituting the group of circulating-water utilization systems.

According to this embodiment, the method further comprises a treatment-vessel moving step of moving a treatment vessel from a purifying unit of a circulating-water utilization system having detected an operational ratio lower than the first threshold to a purifying unit of another circulating-water utilization system having a detected operational ratio greater than the second threshold, and thereby it is possible to efficiently resolve unbalance between supply and demand in a plurality of circulating-water utilization systems which are spread out over a broad region.

In some embodiments, the treatment-vessel moving step comprises moving the treatment-vessel row comprising the plurality of treatment vessels connected in a row.

As described above, treatment vessels are moved in rows in the treatment-vessel moving step, and thereby it is possible to transfer and manage treatment vessels readily for the plurality of circulating-water utilization systems.

Further, at least one embodiment of the present invention is a remote monitoring system for a group of circulating-water utilization systems comprising a plurality of circulating-water utilization systems each of which at least comprises: a circulation channel through which circulating water flows; a discharge channel through which wastewater discharged from a water consumer is discharged to the circulation channel, the water consumer being composed of a plurality of water consuming members including at least one of a residence, a tenant shop, or an office which uses the circulating water flowing through the circulating channel; a purifying unit comprising a treatment-vessel row including a plurality of treatment vessels connected in a row, the treatment vessels comprising containers which house treatment devices configured to perform respective treatment processes which constitute a purifying process of purifying the circulating water containing the wastewater flowing through the circulation channel; and a supply channel configured to supply the circulating water purified by the purifying unit to the water consumer, comprises: an operational-ratio detecting unit capable of detecting operational ratios of the treatment vessels forming the purifying unit of each of the plurality of circulating-water utilization systems constituting the group of circulating-water utilization systems; a data transmitting unit capable of transmitting data related to the operational ratios of the treatment vessels detected by the operational-ratio detecting unit via a transmission line; and a remote monitoring device including a data receiving part capable of receiving the data related to the operational ratios of the treatment vessels transmitted from the data transmitting unit, and a data display part capable of displaying the data related to the operational ratios of the treatment vessels received by the data receiving part.

Accordingly, the remote monitoring system of the group of circulating-water utilization systems comprises: the operational-ratio detecting units capable of detecting the operational ratios of the purifying units in the respective circulating-water utilization systems constituting the group of circulating-water utilization systems; the data transmitting units configured to transmit data related to these operational ratios; and the remote monitoring device including the receiving part capable of receiving the transmitted data and the display part capable of displaying the received data. Thus, it is possible to achieve in real time the basis of determination for moving treatment vessels from a purifying unit of a circulating-water utilization system with a lower operational ratio of treatment vessels to a purifying unit of a circulating-water utilization system with a higher operational ratio of treatment vessels, and thereby it is possible to resolve unbalance between supply and demand among a plurality of circulating-water utilization systems which are spread out over a broad region.

Advantageous Effects

According to at least one embodiment of the present invention, it is possible to provide a method and a system of monitoring a plurality of circulating-water utilization systems remotely, for efficiently resolving unbalance between supply and demand among a plurality of circulating-water utilization systems spread out over a broad region, for launch of the novel circulating-water utilization system in a broad region.

BRIEF DESCRIPTION OF DRAWINGS

FIG. 4 is an explanatory diagram for describing a treatment-vessel moving step according to an embodiment of the present invention.

DETAILED DESCRIPTION

Embodiments of the present invention will now be described in more detail with reference to the accompanying drawings.

However, the scope of the present invention is not limited to the following embodiments. It is intended that dimensions, materials, shapes, relative positions and the like of components described in the embodiments shall be interpreted as illustrative only and not intended to limit the scope of the present invention.

Figure 1:
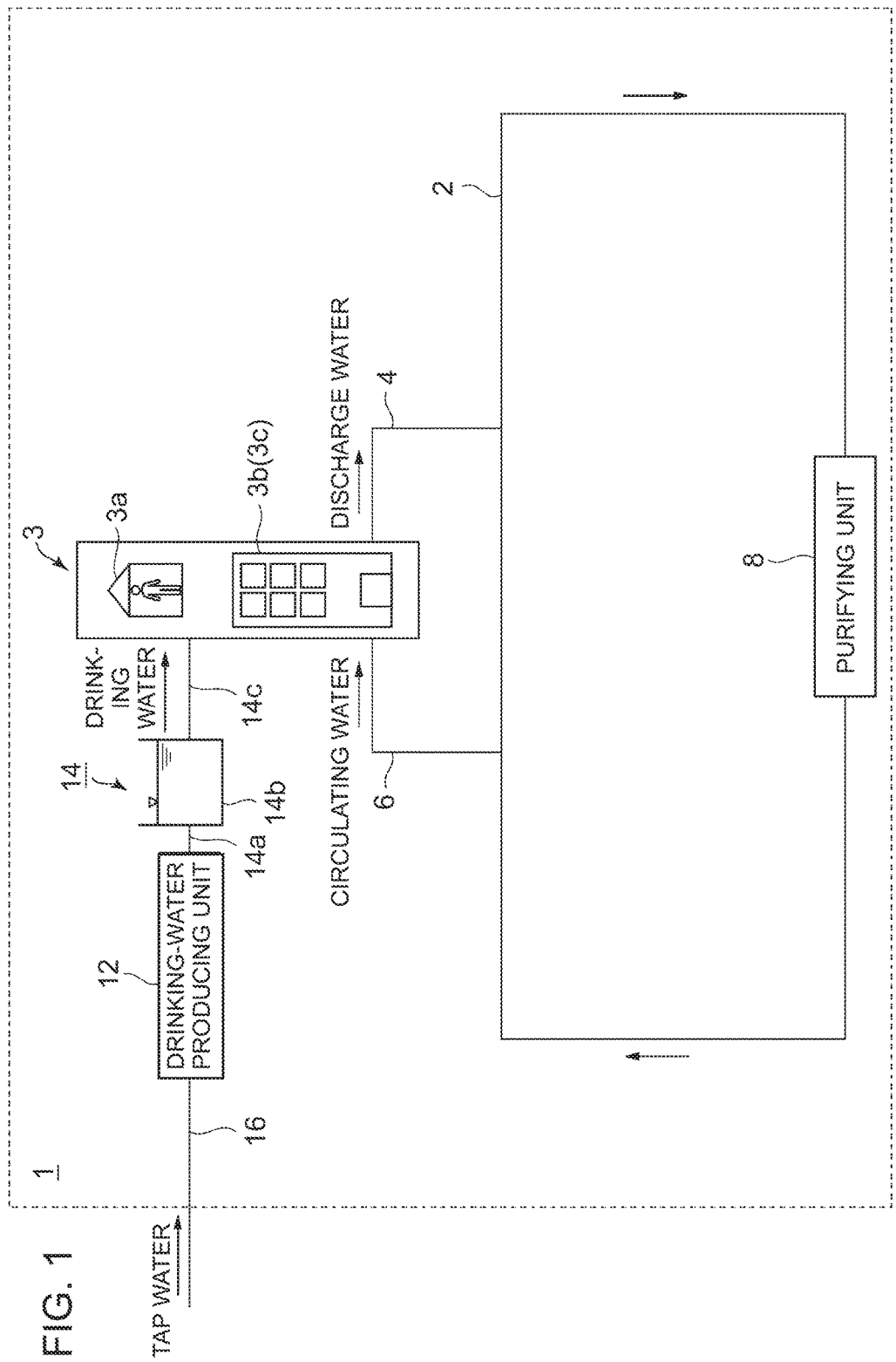
FIG. 1 is an overall schematic diagram of a circulating-water utilization system according to an embodiment of the present invention.

FIG. 1 is an overall schematic diagram of a circulating-water utilization system according to an embodiment of the present invention.

A circulating-water utilization system 1 is constructed in a specific area separately from a public waterworks system. The present system is designed to be applied to a population of approximately 5,000 to 20,000. An area of application is supposed to be an apartment composed of residences, an office building composed of offices, a commercial facility composed of tenant shops, a complex composed of combination of the above, or the like.

As illustrated in FIG. 1, the circulating-water utilization system 1 includes a circulation channel 2, a water consumer 3, a discharge channel 4, a supply channel 6, a purifying unit 8, a drinking-water producing unit 12, and a drinking-water supply unit 14, for instance.

The circulation channel 2 is configured as a piping network of water pipeline arranged in a closed loop. Various devices such as a pump (not depicted) and a valve (not depicted) are disposed where needed in the circulation channel 2 in accordance with terrain conditions or the like, so that circulating water flows circulating in a direction.

Raw water of circulating water that flows through the circulation channel 2 is not limited to tap water supplied from a public waterworks system, and may be well water, river water, rain water, or desalinated sea water, for instance. Further, if circulating water is insufficient, such raw water may be taken into the circulation channel 2 from outside as makeup water. If raw water is taken into the circulation channel 2 as makeup water, the raw water may be taken into treatment vessels of the purifying unit 8 described below in accordance with the water quality level of the raw water. For instance, well water, river water, and desalinated sea water, which have a relatively high water quality, may be taken into a coarse-membrane container L4 or a fine-membrane container L5 of the purifying unit 8 described below, and rain water with a relatively low water quality may be taken into a permeable container L2 or an aerobic container L3.

The water consumer 3 is a subjective member that utilizes circulating water that flows through the circulation channel 2 as daily life water. The water consumer 3 is composed of a plurality of water consuming members including at least one of a residence 3a, a tenant shop 3b, or an office 3c. A residence 3a refers to a unit of an apartment complex or a stand-along house inhabited by a family. A tenant shop 3b refers to a shop or the like which offers services to the general consumer in a section of a commercial facility. The business category of the tenant shops may include, for instance, the retailing business such as clothing stores, grocery stores, drug stores, and alcohol stores, as well as the food-service business such as restaurants, cafes, sushi bars, and pubs. An office 3c refers to a place where employees working at the place do desk work for a certain purpose in a section of an office building, for instance.

In the residence 3a, daily life water is used for shower, bath, washing clothes, washing dishes, washing face and hands, toilet, etc. In the tenant shop 3b, daily life water is used for cleaning, toilet, etc. The amount of water demand is widely varied between different kinds of businesses. For instance, a restaurant uses far more daily life water than a retail store. The office 3c mainly uses daily life water for toilet.

Further, the water consumer 3 is supplied with drinking water separately from the above described circulating water. This drinking water is produced by further purifying tap water introduced from a public waterworks system, and has a quality equivalent to that of mineral waters sold at market. This system can alleviate anxiety of users who may hesitate to drink circulating water, and is expected to provide a selling point for popularizing the present circulating-water utilization system 1.

Tap water is introduced into the drinking-water producing unit 12 from a public water works system via a tap-water introducing channel 16. The drinking-water producing unit 12 produces drinking water for the water consumer 3 by purifying the introduced tap water. The drinking-water producing unit 12 comprises a container-type treatment vessel including a container that houses a processing device that performs a treatment step consisting a series of purifying steps, similarly to the purifying unit 8 described below. The drinking-water producing unit 12 may comprise a plurality of the container-type treatment vessels connected in series along an order of treatment steps.

In the present specification, a container refers to a box-shaped reservoir whose dimensions are standardized for transportation purpose.

It should be noted that raw water of drinking water in the circulating-water utilization system 1 is not limited to tap water, and may be well water, river water, or desalinated sea water, for instance.

Drinking water produced by the drinking-water producing unit 12 is supplied to each water consuming member by the drinking-water supply unit 14. The drinking-water supply unit 14 comprises a drinking-water feeding channel 14a, a reservoir tank 14b, and a drinking-water channel 14c. Drinking water produced by the drinking-water producing unit 12 is fed to the reservoir tank 14b via the drinking-water feeding channel 14a and stored temporarily in the reservoir tank 14b. The drinking water stored in the reservoir tank 14b is supplied to each of the water consuming members including the above described residence 3a, tenant shop 3b, and office 3c via the drinking-water channel 14c.

The discharge channel 4 is a channel for draining wastewater discharged from the water consumer 3 to the circulation channel 2. Wastewater discharged from the discharge channel 4 includes drinking water and water not from the system, in addition to circulating water having been utilized by the water consumer 3 as daily life water. The supply channel 6 is a channel for supplying circulating water purified by the following purifying unit 8 to the water consumer 3 as daily life water. The discharge channel 4 and the supply channel 6 both comprise pipeline. Various devices such as a pump (not depicted) and a valve (not depicted) are disposed where needed in the discharge channel 4 and the supply channel 6 in accordance with terrain conditions or the like, so that wastewater drains to the circulation channel 2, or circulating water is supplied to the water consumer 3.

The purifying unit 8 is a unit to purify circulating water containing waste water that flows through the circulation channel 2. The purifying unit 8 comprises a container-type treatment vessel including a container that houses a processing device that performs a treatment step consisting a series of purifying steps. The drinking-water producing unit 12 may comprise a plurality of the container-type treatment vessels connected in series along an order of treatment steps. The purifying unit 8 of the present embodiment comprises a treatment-vessel row of the following three connected treatment vessels: the first treatment vessel (e.g. the treatment vessel L3 described below) comprising a container housing a treatment device which performs a treatment step which is one of three or more treatment steps into which a series of purifying steps is divided; the second treatment vessel (e.g. the treatment vessel L4 described below) comprising a container housing a treatment device which performs the next treatment step of the treatment step performed by the first treatment vessel; and the third treatment vessel (e.g. the treatment vessel L5 described below) comprising a container housing a treatment device which performs the next treatment step of the treatment step performed by the second treatment vessel.

Further, in the present circulating-water utilization system 1, the circulation channel 2 is not connected to a public sewage system. As described below, excess sludge such as sludge cake produced during purification of waste water is carried out of the system, but otherwise wastewater is re-utilized 100%. In other words, the present circulating-water utilization system 1 is a full-circulation type circulating-water utilization system that supplies and processes water in circulation within the system, and does not discharge sewage water out of the system.

Figure 2:
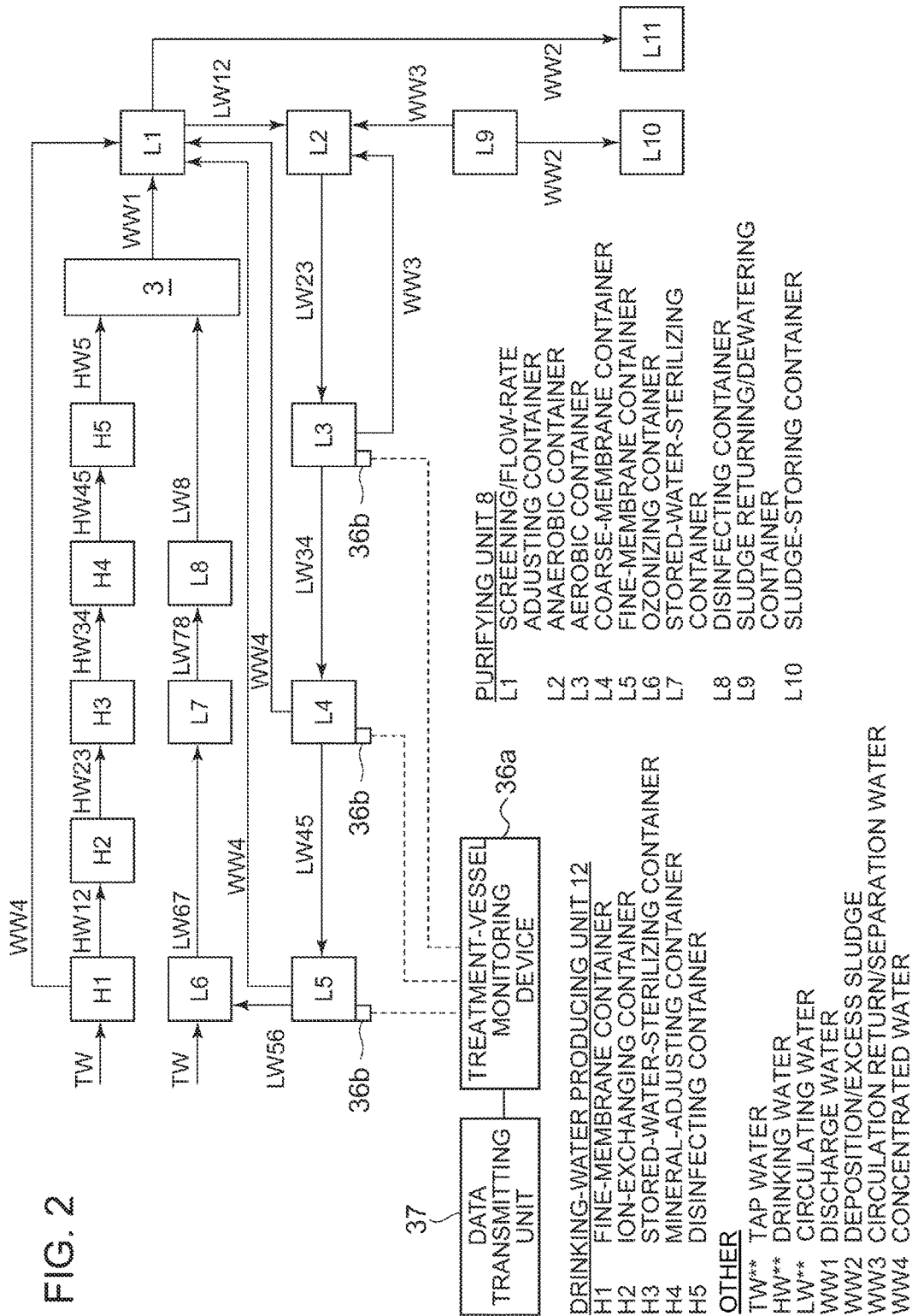
FIG. 2 is a schematic diagram corresponding to the circulating-water utilization system depicted in FIG. 1, showing an example of a layout of treatment vessels of a purifying unit and of a drinking-water producing unit in particular.

FIG. 2 is a schematic diagram corresponding to the circulating-water utilization system depicted in FIG. 1, showing an example of a layout of treatment vessels of a purifying unit and a drinking-water producing unit in particular. In an embodiment illustrated in FIG. 2, the purifying unit 8 comprises a screening/flow-rate-adjusting container L1, an anaerobic container L2, an aerobic container L3, a coarse-membrane container L4, a fine-membrane container L5, an ozonizing container L6, a stored-water-sterilizing container L7, and a disinfecting container L8, connected in series in this order.

The screening/flow-rate-adjusting container L1 is a treatment vessel that removes residue or oil from wastewater, and equipped with an oil trap, a screening device, or the like. The anaerobic container L2 and the aerobic container L3 are treatment vessels for removing organic substances from wastewater by performing an anaerobic treatment and an aerobic treatment. Various known processes may be employed for the treatments, including the A20 activated sludge process, the batch activated sludge process, the contact oxidation process, and the oxidation ditch process, for instance. The coarse-membrane container L4 is a treatment vessel for separating sludge from wastewater. Various devices and processes may be employed, including a settling tank, a MF membrane, a UF membrane, and centrifugal separation, for instance. The fine-membrane container L5 is a treatment vessel for improving the water quality of circulating water to the level of clean water. Various devices and processes may be employed, including a reverse osmosis membrane, activated charcoal, a sand filter, an ozone generator, an ion exchanger, and a mineral adding device, for instance. The ozonizing container L6 is a treatment vessel for ozonizing purified circulating water. The stored-water-sterilizing container L7 is a treatment vessel for storing circulating water temporarily while sterilizing purified circulating water with UV or the like. The disinfecting container L8 is a treatment vessel for disinfecting purified circulating water with UV, chlorine, ozone, or the like.

A sludge-returning/sludge-dewatering container L9 is a treatment vessel for dewatering and drying sludge. Sludge-storing containers L10, L11 are treatment vessels for storing waste produced during sewage treatment. The waste includes, for instance, sludge cake and residue. Excess sludge such as sludge cake stored in the sludge-storing containers L10, L11 are carried out of the system by, for instance, being collected by a fertilizer maker.

Further, in an embodiment illustrated in FIG. 2, the drinking-water producing unit 12 comprises a fine-membrane container H1, an ion-exchanging container H2, a stored-water-sterilizing container H3, a mineral-adjusting container H4, and a disinfecting container H5, connected in series in this order. The fine-membrane container H1, the ion-exchanging container H2, the stored-water-sterilizing container H3, the mineral-adjusting container H4, and the disinfecting container H5 are treatment vessels for further purifying tap water to improve its quality as high as that of mineral waters sold in market.

The fine-membrane container H1 includes various devices and processes such as a reverse osmosis membrane, activated charcoal, and a sand filter, for instance. The ion-exchanging container H2 includes an ion-exchanging device, for instance. The stored-water-sterilizing container H3 is a treatment vessel for storing water temporarily while sterilizing purified tap water with UV or the like. The mineral-adjusting container H4 includes a mineral-adding device, for instance. The disinfecting container H5 is a treatment vessel for disinfecting purified tap water with UV, chlorine, ozone, or the like.

It should be noted that the above described layouts and configurations of the treatment vessels of the purifying unit 8 and the drinking-water producing unit 12 are merely examples, and various modifications may be implemented in accordance with a water quality of wastewater to be discharged or a target purification standard. Further, the reference sign TW in the drawing represents a flow of tap water supplied from a public water works system. Tap water TW may be supplied not only to the drinking-water producing unit 12 as described above, but also to the circulation channel 2 as makeup water if needed. In this case, tap water TW may be supplied at a downstream side of the fine-membrane container L5, where purification of wastewater is nearly completed. Further, the reference sign WW4 in the drawing represents a returning line for feeding concentrated water to the screening/flow-rate-adjusting container L1.

As described above, in the novel circulating-water utilization system 1 being developed by the present applicant, the purifying unit 8 for purifying waste water and the drinking-water producing unit 12 for purifying tap water both comprise container-type treatment vessels which include containers each of which houses a treatment device that performs a treatment step, which is one of three or more treatment steps into which a series of purifying steps is divided. A container-type treatment vessel that performs the first treatment step, a container-type treatment vessel that performs the second treatment step, and a container type treatment vessel that performs the third treatment step are carried into a site, and connected in series via connection piping, and thereby the purifying unit 8 is constructed. Such a container-type treatment vessel can be loaded onto a truck to be transported as it is, and thus has a high transportability. Further, such a container-type treatment vessel is housed in a container housing removably, and thus can be installed and removed as desired.

With regard to processing capacity, the above container-type treatment vessels are each supposed to be capable of processing wastewater from approximately 1,000 persons. Thus, to introduce the present circulating-water utilization system to an area or a complex inhabited by as many as 10,000 persons, for instance, a plurality of (e.g. ten) treatment vessels that performs the same treatment process is required. With a plurality of treatment vessels that performs the same treatment process provided as described above, it is possible to reduce processing capacity per treatment vessel. Thus, it is possible to flexibly address population variation in a target area or seasonal variation of water demand. Further, a substitute treatment vessel can be prepared readily, and maintainability is improved.

Figure 3:
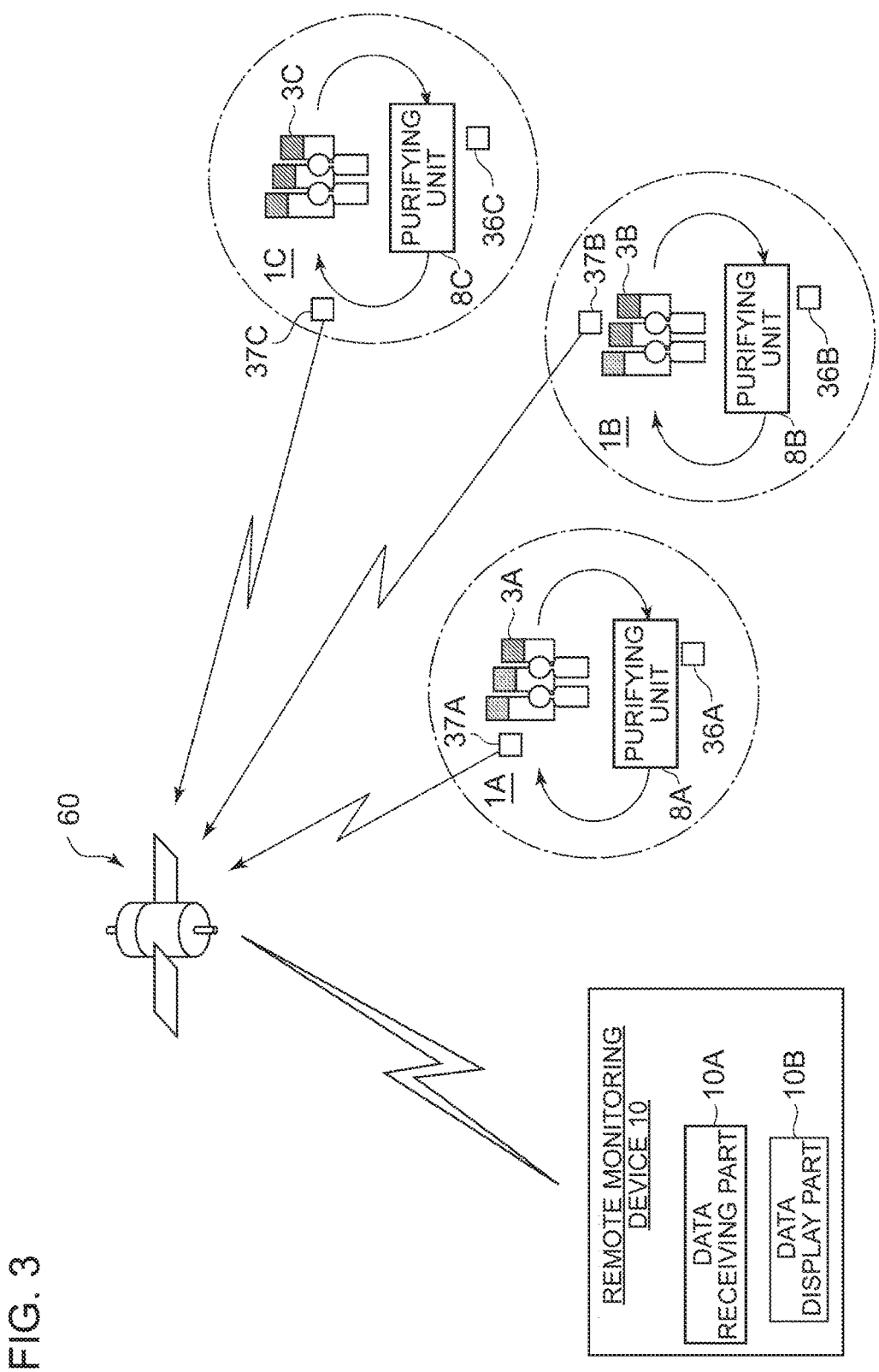
FIG. 3 is an overall schematic diagram for describing a method and a system of monitoring a group of circulating-water utilization systems remotely according to an embodiment of the present invention.
Figure 5:
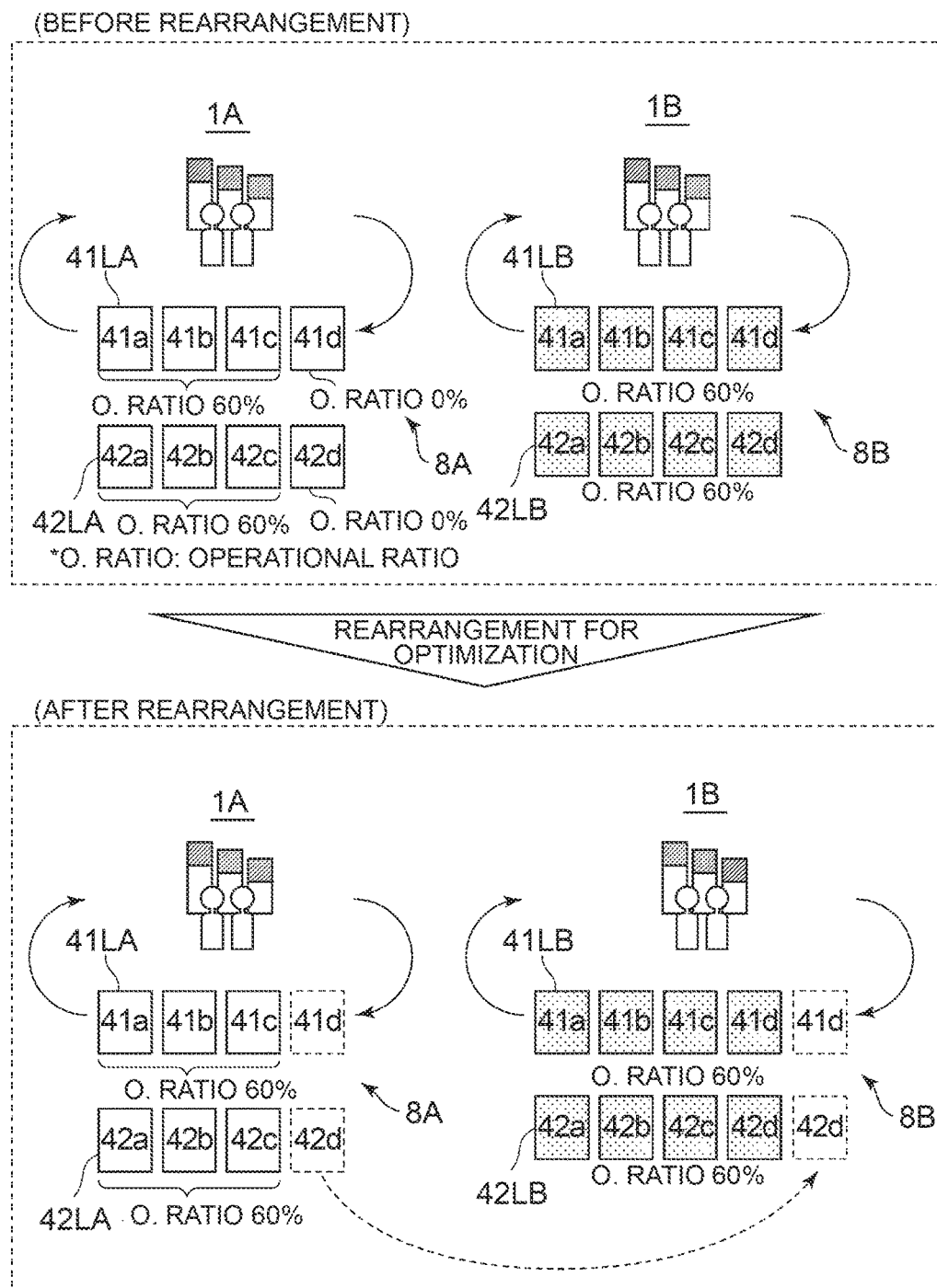
FIG. 5 is an explanatory diagram for describing a treatment-vessel moving step according to an embodiment of the present invention.

FIG. 3 is an overall schematic diagram for describing a method and a system of monitoring a group of circulating-water utilization systems remotely according to an embodiment of the present invention.

As depicted in FIG. 3, a group of circulating-water utilization systems according to an embodiment of the present invention comprises a plurality of the above described circulating-water utilization systems 1A, 1B, 1C provided so as to spread out over a broad region. A remote monitoring device 10 is a device for monitoring the spread out circulating-water utilization systems remotely. The reference signs 3A, 3B, and 3C in the drawing represent respective water consumers in the plurality of circulating-water utilization systems 1A, 1B, and 1C, and the reference signs 8A, 8B, and 8C respective purifying units.

While the plurality of treatment vessels L1 to L8 constituting the purifying unit 8 will be described as an example below, the description can be applied to the plurality of treatment vessels H1A to H5 constituting the drinking-water producing unit.

Further, a remote monitoring system of a group of circulating-water utilization systems comprises, as illustrated in FIG. 1, operational-ratio detecting units 36A, 36B, 36C capable of respectively detecting operational ratios of a plurality of treatment vessels L1 to L8 constituting purifying units 8A, 8B, 8C of the plurality of circulating-water utilization systems 1A, 1B, 1C, and data-transmitting units 37A, 37B, 37C capable of transmitting data related to the operational ratios of the plurality of treatment vessels L1 to L8 detected by the operational-ratio detecting units 36A, 36B, 36C via a transmission line 60 such as a mobile-phone line and a wireless LAN network. The operational-ratio detecting units 36A, 36B, 36C and the data transmitting units 37A, 37B, 37C are disposed respectively in the circulating-water utilization systems 1A, 1B, 1C.

As depicted in FIG. 2, the operational-ratio detecting unit 36 comprises a treatment-vessel monitoring device 36a configured as a microcomputer including a central processing unit (CPU), a random access memory (RAM), a read only memory (ROM), and an I/O interface, and an operational-ratio sensor 36b configured to detect an operational ratio of each of the plurality of treatment vessels L1 to L8. The operational-ratio sensors 36b are disposed on all of the treatment vessels L1 to L8, and data related to respective operational ratios of the treatment vessels detected by the operational-ratio sensors 36b is transmitted to a treatment-vessel monitoring device 36a disposed at a distance from the purifying unit 8 via wire or wirelessly. The transmitted data related to the operational ratio of each treatment vessel is displayed on a display part of the treatment-vessel monitoring device 36a, and is transmitted to the remote monitoring device 10 in a remote place by a data transmitting unit 37.

Herein, an operational ratio of a treatment vessel can be defined as a ratio of a flow rate of water being actually processed to a flow rate of a rated processing capacity of the treatment vessel.

The remote monitoring device 10 is configured as a microcomputer including a central processing unit (CPU), a random access memory (RAM), a read only memory (ROM), and an I/O interface. As depicted in FIG. 3, the remote monitoring device 10 comprises a data receiving part 10A capable of receiving data related to respective operational ratios of the plurality of treatment vessels L1 to L8 transmitted from the data transmitting unit 37, and a data display part 10B capable of displaying data related to the operational ratios of the plurality of treatment vessels L1 to L8 received by the data receiving part 10A. Data related to the operational ratios of the plurality of treatment vessels L1 to L8 constituting each of the purifying units 8A, 8B, 8C is transmitted from the data transmitting units 37A, 37B, 37C disposed respectively on the circulating-water utilization systems 1A, 1B, 1C, and displayed collectively on the data display part 10B.

Accordingly, the remote monitoring system of a group of circulating-water utilization systems comprises: the operational-ratio detecting units 36A, 36B, 36C capable of detecting the operational ratios of the treatment vessels of the purifying units 8A, 8B, 8C in the respective circulating-water utilization systems 1A, 1B, 1C constituting the group of circulating-water utilization systems; the data transmitting units 37A, 37B, 37C configured to transmit data related to these operational ratios, and the remote monitoring device 10 including the data receiving part 10A capable of receiving the transmitted data and the data display part 10B capable of displaying the received data.

Thus, as illustrated in FIG. 4 for instance, it is possible to achieve in real time the basis of determination for moving a treatment vessel from a purifying unit of a circulating-water utilization system with a lower operational ratio of treatment vessels to a purifying unit of a circulating-water utilization system with a higher operational ratio of treatment vessels. In the embodiment depicted in FIG. 4, before rearrangement, the operational ratio of treatment-vessel rows 41LA, 42LA in the purifying unit 8 of the circulating-water utilization system 1A is 30% each, and that of treatment-vessel rows 41LB, 42LB, 43LB in the purifying unit 8B of the circulating-water utilization system 1B is 100% each. In contrast, after rearrangement, the treatment-vessel row 42LA is moved from the purifying unit 8A of the circulating-water utilization system 1A with a lower operational ratio of treatment vessels to the purifying unit 8B of the circulating-water utilization system 1B with a higher operational ratio of treatment vessels, and thereby the operational ratio of the treatment-vessel row 41LA in the purifying unit 8 of the circulating-water utilization system 1A increases to 60%, while the operational ratio of the treatment-vessel rows 41LB, 42LB, 43LB of the purifying unit 8 of the circulating-water utilization system 1B decreases to 75% each, which makes it possible to equalize the operational ratios between the circulating-water utilization systems.

Accordingly, moving a treatment vessel from a purifying unit of a circulating-water utilization system with a lower operational ratio of treatment vessels to a purifying unit of a circulating-water utilization system with a higher operational ratio of treatment vessels makes it possible to efficiently resolve unbalance between supply and demand in a plurality of circulating-water utilization systems which are spread out over a broad region.

Here, a threshold may be provided as a guideline of an operational ratio in moving the treatment vessels. For instance, the first threshold (e.g. 40%) and the second threshold (e.g. 80%) greater than the first threshold may be set in advance, and a treatment-vessel row may be moved from a purifying unit of a circulating-water utilization system having a detected operational ratio lower than the first threshold (e.g. 40%) to a purifying unit of another circulating-water utilization system having a detected operational ratio greater than the second threshold (e.g. 80%), and thereby it is possible to efficiently resolve unbalance between supply and demand in a plurality of circulating-water utilization systems spread out over a broad region.

In the above embodiment, the whole treatment-vessel row 42LA in the purifying unit 8A of the circulating-water utilization system 1A is moved. As described above, moving treatment vessels in rows makes it possible to transfer and manage treatment vessels readily for the plurality of circulating-water utilization systems.

Figure 6:
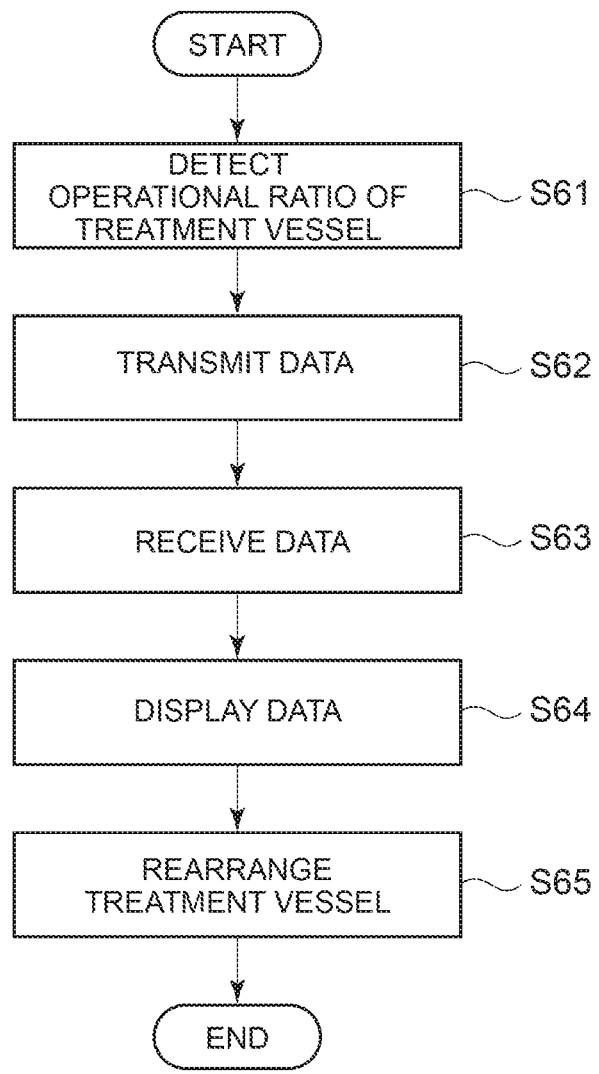
FIG. 6 is a flowchart for describing a method of monitoring a group of circulating-water utilization systems remotely according to an embodiment of the present invention.

However, the present invention is not limited to this, and as depicted in FIG. 6 for instance, only a part of treatment vessels consisting a row of treatment vessels may be moved.

In the embodiment depicted in FIG. 6, in the purifying unit 8A of the circulating-water utilization system 1A, while the treatment-vessel row 41LA comprises the plurality of treatment vessels 41*a*, 41*b*, 41*c*, 41*d* and the treatment-vessel row 42LA comprises the plurality of treatment vessels 42*a*, 42*b*, 42*c*, 42*d*, the treatment vessels 41*d*, 42*d* have an operational ratio of 0% and are not in operation. This is because wastewater discharged from the circulating-water utilization system 1A does not need to be purified by the treatment vessels 41*d*, 42*d* due to the water quality of the wastewater. Meanwhile, in the purifying unit 8B of the circulating-water utilization system 1B, the treatment vessels 41*d*, 42*d* are also operating at an operational ratio of 60%, similarly to the treatment vessels 41*a* to 41*c*, 42*a* to 42*c*.

In this case, moving the treatment vessels 41*d*, 42*d* from the purifying unit 8A of the circulating-water utilization system 1A to the purifying unit 8B of the circulating-water utilization system 1B makes it possible to make efficient use of the treatment vessels 41*d*, 42*d*, which are not in operation, and to increase the water quality level of circulating water in the circulating-water utilization system 1B.

FIG. 6 is a flowchart for describing a method of monitoring a group of circulating-water utilization systems remotely according to an embodiment of the present invention.

As depicted in FIG. 6, a method of monitoring a group of circulating-water utilization systems remotely according to an embodiment of the present invention comprises step S61 (operational-ratio detection step) of detecting operational ratios of a plurality of treatment vessels constituting treatment-vessel rows of each of the purifying units 8A, 8B, 8C in the plurality of circulating-water utilization systems 1A, 1B, 1C constituting the group of circulating-water utilization systems. The operational ratios are detected by the above described operational-ratio detecting units 36.

Next, in step S62 (data transmission step), data related to the operational ratios of the plurality of treatment vessels detected in step S61 is transmitted to the remote monitoring device 10 disposed in a remote place via the transmission line 60.

Next, in step S63 (data reception step), data related to the operational ratios of the plurality of treatment vessels transmitted in step S62 is received by the data receiving part 10A of the remote monitoring device 10.

Next, in step S64 (data display step), data related to the operational ratios of the plurality of treatment vessels received in step S63 is displayed by the data display part 10B of the remote monitoring device 10.

Finally, in step S65 (treatment-vessel moving step), on the basis of the data related to the operational ratios of the plurality of treatment vessels displayed in step S64, a treatment vessel is moved from a purifying unit of a circulating-water utilization system having a lower operational ratio to a purifying unit of another circulating-water utilization system having a higher operational ratio.

As described above, according to the method of monitoring a group of circulating-water utilization systems remotely, it is possible to resolve unbalance between supply and demand among a plurality of circulating-water utilization systems spread out over a broad region.

Connection of Treatment Vessels

Now, from among the treatment vessels L1 to L8 performing a series of purifying steps for purifying wastewater, an optional treatment vessel (e.g. L3) will be referred to as the first treatment vessel, a treatment vessel (e.g. L4) that performs the next treatment step of the treatment step of the first treatment vessel as the second treatment vessel, and a treatment vessel (e.g. L5) that performs the next treatment step of the treatment step of the second treatment vessel as the third treatment vessel. Further, each of the first treatment vessel, the second treatment vessel, and the third treatment vessel comprises a plurality of treatment vessels, and referred to as the first group of treatment vessels, the second group of treatment vessels, and the third group of treatment vessels, respectively.

Figure 7A:
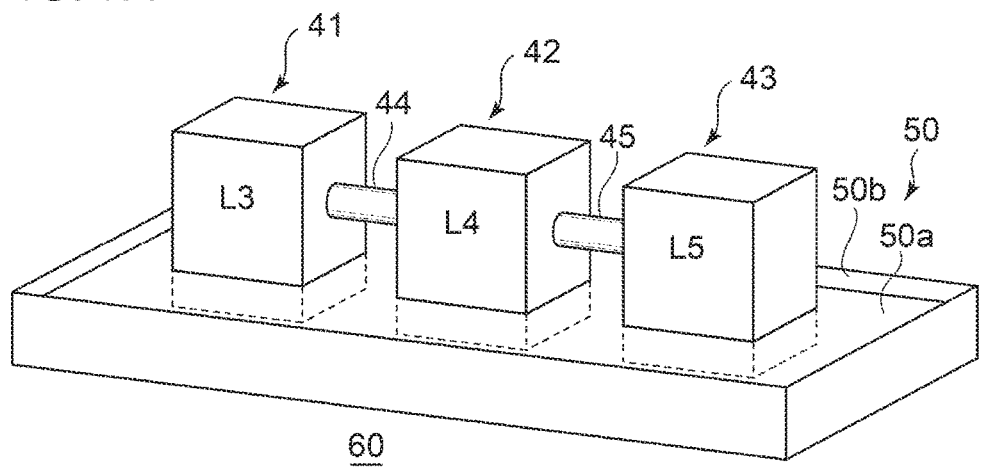
FIGS. 7A and 7B are schematic diagrams of the first treatment vessel, the second treatment vessel, the third treatment vessel, and a container housing which houses these treatment vessels.
Figure 7B:
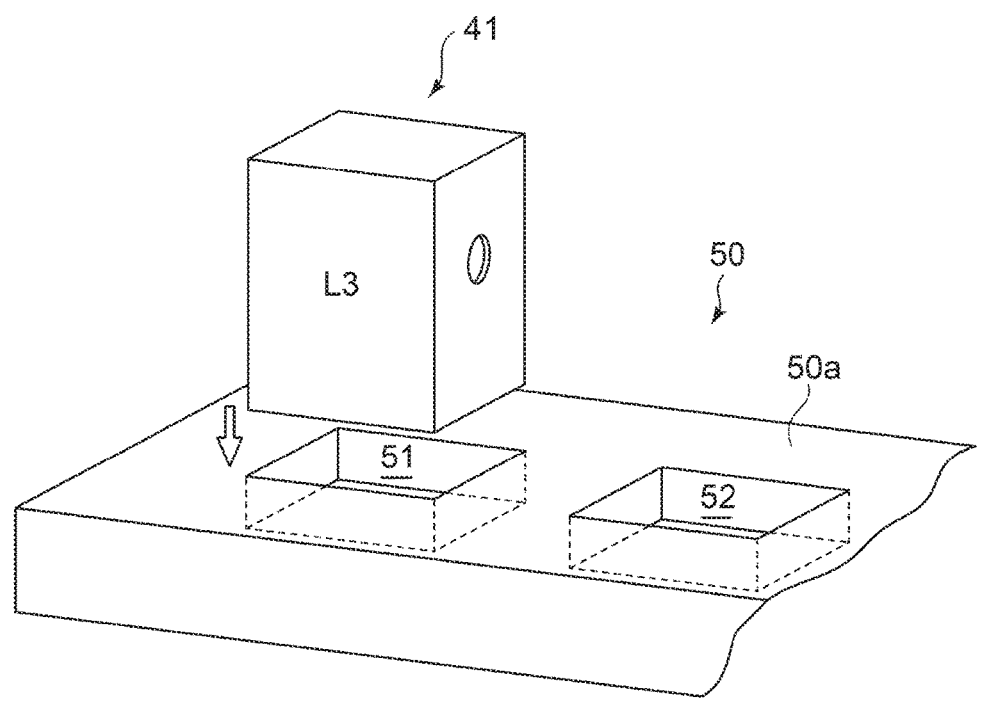
Figure 8A:
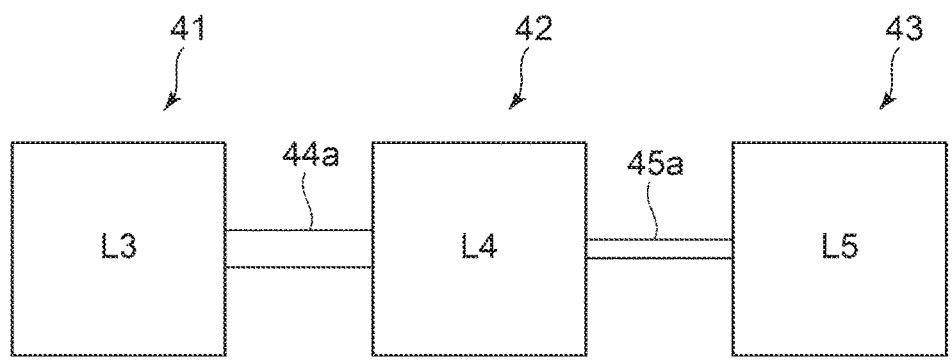
FIGS. 8A and 8B are schematic diagrams for describing connection aspects of the first, second, and third treatment vessels.
Figure 8B:
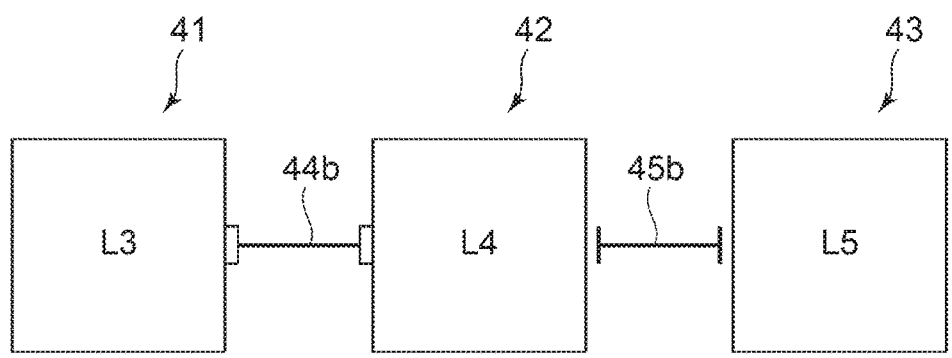

FIGS. 7A and 7B are schematic diagrams of the first treatment vessel, the second treatment vessel, the third treatment vessel, and a container housing which houses these treatment vessels. FIGS. 8A and 8B are schematic diagrams for describing connection aspects of the first, second, and third treatment vessels.

As illustrated in FIGS. 7A and 7B, the first treatment vessel 41, the second treatment vessel 42, and the third treatment vessel 43 are each housed in the container housing 50 removably. The first treatment vessel 41 and the second treatment vessel 42 are connected to each other by the first-to-second connection pipe 44. Further, the second treatment vessel 42 and the third treatment vessel are connected to each other by the second-to-third connection pipe 45.

As illustrated in FIGS. 8A and 8B, the first-to-second connection pipe 44 and the second-to-third connection pipe 45 are different in at least one of pipe diameter, coupling structure, or pipe color. In the embodiment depicted in FIG. 8A, the first-to-second connection pipe 44a has a larger diameter than the second-to-third connection pipe 45, and thus the pipes have different diameters. It should be noted that, in the present invention, an aspect with connection parts having different diameters may include an aspect in which the first-to-second connection pipe 44a and the second-to-third connection pipe 45 have the same diameters and diameters are differentiated only at connection parts by providing adapters. Further, in the embodiment depicted in FIG. 8B, the coupling structure of the first-to-second connection pipe 44b is a socket-and-spigot type coupling, while the coupling structure of the second-to-third connection pipe 45b is a flange coupling, thus having different coupling structures.

As described above, the purifying unit 8 of the circulating-water utilization system 1 is configured such that a series of purifying steps is performed by a plurality of kinds of treatment vessels (the first treatment vessel 41, the second treatment vessel 42, and the third treatment vessel 43) which perform different treatments connected in series via the first-to-second connection pipe 44 and the second-to-third connection pipe 45. If the plurality of kinds of treatment vessels are connected in a wrong order, a series of purifying steps may fail to be performed correctly, thus resulting in a failure in function of the purifying unit 8. Thus, in the purifying unit 8 of the circulating-water utilization system 1, the first-to-second connection pipe 44 connecting the first treatment vessel 41 and the second treatment vessel 42 is differentiated from the second-to-third connection pipe 45 connecting the second treatment vessel 42 and the third treatment vessel 43 at least in one of the pipe diameter of the connection parts, the coupling structure, or the pipe color, so as to prevent incorrect pipe arrangement between different kinds of treatment vessels.

In the above embodiment, preferably, one of pipe diameter or coupling structure may be different in addition to pipe color. Pipe colors can function as discriminating markers, but cannot physically impede errors in pipe connection. Conversely, with one of pipe diameter or coupling structure being different, it is possible to prevent errors in pipe connection between different kinds of treatment vessels physically and securely.

Further, in the above embodiment, with adapters connected to the first-to-second connection pipe and the second-to-third connection pipe so that the pipes with different pipe diameters are connectible, it is possible to flexibly address special combinations such as connection of the first treatment vessel and the third treatment vessel.

Figure 9:
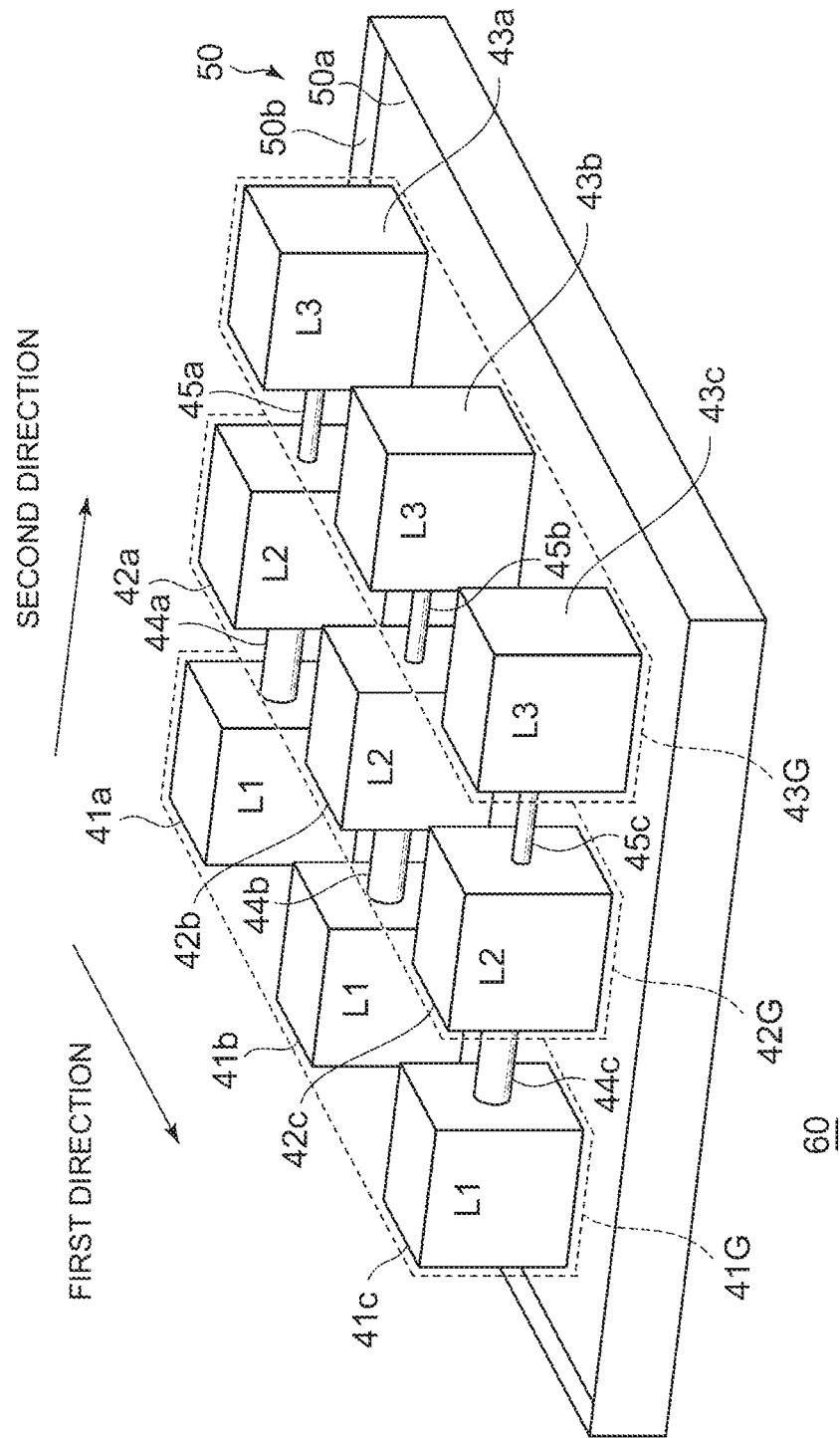
FIG. 9 is a schematic diagram of the first group of treatment vessels, the second group of treatment vessels, the third group of treatment vessels, and a container housing which houses these groups of treatment vessels.
Figure 10:
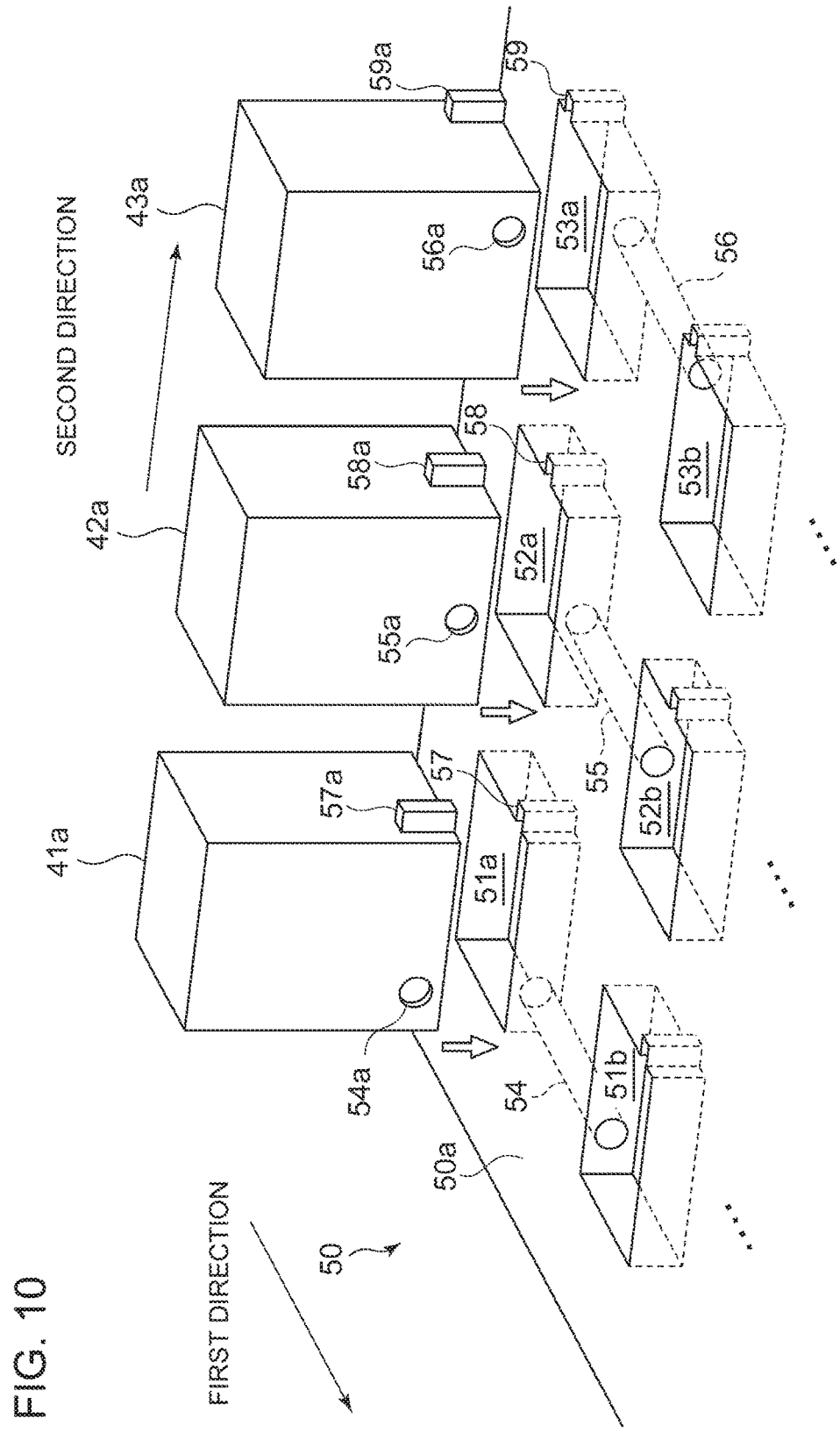
FIG. 10 is a diagram for describing a connection aspect between a group of the same treatment vessels disposed in a direction.

FIG. 9 is a schematic diagram of the first group of treatment vessels, the second group of treatment vessels, the third group of treatment vessels, and a container housing which houses these groups of treatment vessels. FIG. 10 is a diagram for describing a connection aspect between a group of the same treatment vessels disposed in a direction.

In some embodiments, as depicted in FIG. 9, the first treatment vessels 41, the second treatment vessels 42, and the third treatment vessels 43 have the same exterior shape. Further, as illustrated in FIG. 10, the container housing 50 comprises a base 50a and a plurality of rectangular recesses 51, 52, 53 formed on the base 50a. Furthermore, the plurality of recesses are disposed to form rows in the first direction of the base 50a and in the second direction orthogonal to the first direction. Between the recesses disposed in a row in the first direction, water channels 54, 55, 56 are formed so as to bring adjacent recesses (recesses 51a and 51b recesses 52a and 52b, recesses 53a and 53b) into communication. Further, as illustrated in FIG. 10, a plurality of treatment vessels which perform the same treatment process is fitted into corresponding one of the rows of the recesses disposed in the first direction. The plurality of treatment vessels includes the first treatment-vessel group 41G comprising the first treatment vessels 41a, 41b, 41c, the second treatment-vessel group 42G comprising the second treatment vessels 42a, 42b, 42c, and the third treatment-vessel group 43G comprising the third treatment vessels 43a, 43b, 43c. The first treatment vessel 41, the second treatment vessel 42, and the third treatment vessel 43 are fitted in this order into the plurality of recesses disposed in the second direction. The plurality of treatment vessels which perform the same treatment process is connected so that water is communicable via the water channels 54, 55, 56.

According to this embodiment, containers of the first treatment vessels 41, the second treatment vessels 42, and the third treatment vessels 43 all have the same exterior shape, and thus can be readily produced and handled. A plurality of treatment vessels which perform the same treatment process is fitted into the plurality of recesses disposed in the first direction, and the first treatment vessel 41, the second treatment vessel 42, and the third treatment vessel 43 are fitted in this order into the plurality of recesses disposed in the second direction. The plurality of treatment vessels which perform the same treatment process is connected so that water is communicable via the water channels 54, 55, 56 formed in the base 50a. Thus, to increase the number of treatment vessels temporarily to address seasonal variation of water demand, deterioration of water quality of wastewater, or the like, the treatment vessels can be connected so that water is communicable, only by fitting treatment vessels which perform the same treatment process into recesses disposed in the first direction. Thus, additional treatment vessels can be provided readily, which makes it possible to flexibly address seasonal variation of water demand, deterioration of water quality of purified water, and the like.

In some embodiments, as depicted in FIG. 10, openings 54a, 55a, 56a connecting to the water channels 54, 55, 56 are formed on positions different between the first treatment vessel 41a, the second treatment vessel 42a, and the third treatment vessel 43a, on the side surfaces of respective containers of the first treatment vessel 41a, the second treatment vessel 42a, and the third treatment vessel 43a. The water channels 54, 55, 56 are formed on positions different between the recesses 51a, 52a, 53a, into which the first treatment vessel 41a, the second treatment vessel 42a, and the third treatment vessel 43a are to be inserted respectively, so that an opening of a treatment vessel and a water channel of a recess connect to each other only if the treatment vessel is fit into the corresponding recess.

Specifically, in the depicted embodiment, the opening 54a of the side surface of the container of the first treatment vessel 41a is formed on a position on the left side of the side surface so as to connect to the water channel 54 if the first treatment vessel 41a is inserted into the corresponding recess 51a. The opening 55a of the side surface of the container of the second treatment vessel 42a is formed on a position in the middle of the side surface so as to connect to the water channel 55 if inserted into the corresponding recess 52a. The opening 56a of the side surface of the container of the third treatment vessel 43a is formed on a position on the right of the side surface so as to connect to the water channel 56 if inserted into the corresponding recess 53a. Further, the water channel 54 is formed through the left portion between the recesses 51a, 51b. The water channel 55 is formed through the middle portion between the recesses 52a, 52b. The water channel 56 is formed through the right portion between the recesses 53a, 53b.

According to this embodiment, an opening and a water channel are connected only if a treatment vessel is fitted into a corresponding recess. Thus, even if the second treatment vessel 42a is fitted into the recess 51a originally designed to be engaged with the first treatment vessel 41a, the opening 55a of the second treatment vessel 42a would not connect to the water channel 54. Thus, with the above configuration, it is possible to prevent errors in connection of treatment vessels securely.

In some embodiments, as depicted in FIG. 9, mating recesses 57, 58, 59 are formed on opening rims of the recesses 51a, 52a, 53a, and mating projections 57a, 58a, 59a to be mated with the mating recesses 57, 58, 59 are formed on the side surfaces of respective containers of the first treatment vessel 41a, the second treatment vessel 42a, and the third treatment vessel 43a, at positions varied between the first treatment vessel 41a, the second treatment vessel 42a, and the third treatment vessel 43a. The mating recesses 57, 58, 59 are formed on positions different between the recesses 51a, 52a, 53a, into which the first treatment vessel 41a, the second treatment vessel 42a, and the third treatment vessel 43a are to be inserted respectively, so that a mating projection mates with a mating recess and a treatment vessel is fitted into a corresponding recess only if the treatment vessel and the recess correspond to each other.

Specifically, in the depicted embodiment, the mating projection 57a of the side surface of the container of the first treatment vessel 41a is formed on a position closer to the front. The mating projection 58a of the side surface of the container of the second treatment vessel 42a is formed on a position in the middle. The mating projection 59a of the side surface of the container of the third treatment vessel 43a is formed on a position closer to the back.

Further, the mating recess 57 of the recess 51a into which the first treatment vessel 41a is to be fitted is formed on a position closer to the front of the opening rim. The mating recess 58 of the recess 52a into which the second treatment vessel 42a is to be fitted is formed on a position in the middle of the opening rim. The mating recess 59 of the recess 53a into which the third treatment vessel 43a is to be fitted is formed on a position closer to the back of the opening rim.

According to this embodiment, a mating projection formed on a side surface of a container mates with a mating recess formed on an opening rim of a recess only if a treatment vessel is fitted into the corresponding recess. Thus, the second treatment vessel 42a cannot be fitted into the recess 51a designed to be engaged with the first treatment vessel 41a, interrupted by the mating projection 58a formed on the side surface of the container. Thus, with the above configuration, it is possible to prevent incorrect connection of treatment vessels securely.

The embodiments of the present invention have been described above. However, the present invention is not limited thereto. For instance, various modifications may be applied as long as they do not depart from the object of the present invention.

INDUSTRIAL APPLICABILITY

At least an embodiment of the present invention can be suitably applied as a circulating-water utilization system to be constructed in a specific area separately from a public waterworks system.

DESCRIPTION OF REFERENCE NUMERALS

1 Circulating-water utilization system
2 Circulation channel
3 Water consumer
3a Residence
3b Tenant shop
3c Office
4 Discharge channel
6 Supply channel
8 Purifying unit (purifying device)
8a Purifying-unit control unit
10 Remote monitoring device
10A Data receiving part
10B Data display part
12 Drinking-water producing unit
14 Drinking-water supply unit
14a Drinking-water feeding channel
14b Reservoir tank, drinking-water tank
14c Drinking-water channel
16 Tap-water introducing channel
36 Operational-ratio detecting unit
36a Treatment-vessel monitoring device
36b Operational-ratio sensor
37 Data transmitting unit
41 First treatment vessel
41G First treatment-vessel group
42 Second treatment vessel
42G Second treatment-vessel group
43 Third treatment vessel
43G Third treatment-vessel group
44 First-to-second connection pipe
45 Second-to-third connection pipe
50 Container housing
50a Base
51 Recess
54, 55, 56 Water channel
54a, 54b, 54c Opening
57, 58, 59 Mating recess
57a, 58a, 59a Mating projection
60 Transmission line

The invention claimed is:

1. A method of remotely monitoring a group of circulating-water utilization systems including a plurality of circulating-water utilization systems each of which at least includes a circulation channel through which circulating water flows, a discharge channel through which wastewater discharged from a water consumer is discharged to the circulation channel, the water consumer being composed of a plurality of water consuming members including at least one of a residence, a tenant shop, or an office which uses the circulating water flowing through the circulating channel, a purifying unit including a treatment-vessel row including a plurality of treatment vessels connected in a row, the treatment vessels including containers which house treatment devices configured to perform respective treatment processes which constitute a purifying process of purifying the circulating water containing the wastewater flowing through the circulation channel, and a supply channel configured to supply the circulating water purified by the purifying unit to the water consumer, the method comprising:
- an operational-ratio detection step of detecting operational ratios of the treatment vessels forming the treatment-vessel row of the purifying unit, for each of the plurality of circulating-water utilization systems constituting the group of circulating-water utilization systems;
- a data transmission step of transmitting data related to the operational ratios of the treatment vessels detected in the operational-ratio detection step via a transmission line;
- a data reception step of receiving the data related to the operational ratios of the treatment vessels transmitted in the data transmission step;
- a data display step of displaying the data related to the operational ratios of the treatment vessels received in the data reception step, and
- a treatment-vessel moving step of moving the treatment vessel from the purifying unit of one of the circulating-water utilization systems having a detected operational ratio lower than a first threshold set in advance, to the purifying unit of another one of the circulating-water utilization systems having a detected operational ratio higher than a second threshold which is set to be greater than the first threshold, from among the plurality of circulating-water utilization systems constituting the group of circulating-water utilization systems.

2. The method of remotely monitoring a group of circulating-water utilization systems according to claim 1,
- wherein the treatment-vessel moving step comprises moving the treatment-vessel row comprising the plurality of treatment vessels connected in a row.

3. A remote monitoring system for a group of circulating-water utilization systems comprising a plurality of circulating-water utilization systems each of which at least comprises:
- a circulation channel through which circulating water flows;
- a discharge channel through which wastewater discharged from a water consumer is discharged to the circulation channel, the water consumer being composed of a plurality of water consuming members including at least one of a residence, a tenant shop, or an office which uses the circulating water flowing through the circulating channel;
- a purifying unit comprising a treatment-vessel row including a plurality of treatment vessels connected in a row, the treatment vessels comprising containers which house treatment devices configured to perform respective treatment processes which constitute a purifying process of purifying the circulating water containing the wastewater flowing through the circulation channel; and
- a supply channel configured to supply the circulating water purified by the purifying unit to the water consumer, the remote monitoring system comprising:
- an operational-ratio detecting unit capable of detecting operational ratios of the treatment vessels forming the purifying unit of each of the plurality of circulating-water utilization systems constituting the group of circulating-water utilization systems;
- a data transmitting unit capable of transmitting data related to the operational ratios of the treatment vessels detected by the operational-ratio detecting unit via a transmission line; and
- a remote monitoring device including a data receiving part capable of receiving the data related to the operational ratios of the treatment vessels transmitted from the data transmitting unit, and a data display part capable of displaying the data related to the operational ratios of the treatment vessels received by the data receiving part,
wherein the treatment vessel is capable of being moved from the purifying unit of one of the circulating-water utilization systems having a detected operational ratio lower than a first threshold set in advance, to the purifying unit of another one of the circulating-water utilization systems having a detected operational ratio higher than a second threshold which is set to be greater than the first threshold, from among the plurality of circulating-water utilization systems constituting the group of circulating-water utilization systems.

* * * * *